(12) United States Patent
Revie et al.

(10) Patent No.: US 7,585,302 B2
(45) Date of Patent: Sep. 8, 2009

(54) INSTRUMENT FOR IMPLANTING A SENSOR

(75) Inventors: Ian Revie, Boroughbridge (GB); Yaacov Nitzan, Tel-Aviv (IL); Jury Baldewein, Munich (DE)

(73) Assignee: Depuy International Ltd., Leeds (GB)

( * ) Notice: Subject to any disclaimer, the term of this patent is extended or adjusted under 35 U.S.C. 154(b) by 405 days.

(21) Appl. No.: 11/063,018

(22) Filed: Feb. 22, 2005

(65) Prior Publication Data
US 2006/0190009 A1    Aug. 24, 2006

(51) Int. Cl.
*A61B 19/00* (2006.01)
(52) U.S. Cl. .................. 606/129; 600/424; 600/184
(58) Field of Classification Search .............. 606/129; 600/566, 567, 424
See application file for complete search history.

(56) References Cited

U.S. PATENT DOCUMENTS

| | | | |
|---|---|---|---|
| 4,799,495 A | | 1/1989 | Hawkins |
| 5,478,343 A | | 12/1995 | Ritter |
| 5,595,193 A | * | 1/1997 | Walus et al. ............... 128/898 |
| 5,665,092 A | * | 9/1997 | Mangiardi et al. ............ 606/86 |
| 5,667,514 A | * | 9/1997 | Heller ....................... 606/108 |
| 5,895,390 A | | 4/1999 | Moran |
| 6,036,696 A | | 3/2000 | Lambrecht |
| 6,074,394 A | | 6/2000 | Krause |
| 6,499,488 B1 | | 12/2002 | Hunter |
| 6,801,809 B2 | | 10/2004 | Laske |
| 2003/0120150 A1 | | 6/2003 | Govari |
| 2004/0034355 A1 | | 2/2004 | Govari |
| 2004/0153098 A1 | * | 8/2004 | Chin et al. .................. 606/129 |
| 2006/0224109 A1 | * | 10/2006 | Steil et al. .................... 604/66 |
| 2007/0276288 A1 | * | 11/2007 | Khaw .......................... 600/566 |

FOREIGN PATENT DOCUMENTS

EP    702933  A1    3/1996

* cited by examiner

*Primary Examiner*—Todd E Manahan
*Assistant Examiner*—Jennifer L Hornberger

(57) ABSTRACT

An instrument for implanting a sensor in a body part, in which the sensor has at least one cord extending therefrom which is connected to an external device, includes a guide sheath for defining a path to the surface of the body part through overlaying soft tissue, the sheath having a bore extending along its length between first and second open ends through which the tool can pass and a slot that extends along its length between its first and second open ends. A delivery sheath for implanting the sensor in the hole has a bore extending along its length between a first open end at which the sensor can be mounted and a second end, with the cord extending from the sensor along the bore, in which the sheath has a slot that extends along its length between its first and second end, and wherein the delivery sheath can be received within the guide sheath by sliding the delivery sheath within the bore of the guide sheath. The slots of the guide and delivery sheaths can be aligned to allow the cord to be removed from the bores other than at the ends of the bores.

13 Claims, 7 Drawing Sheets

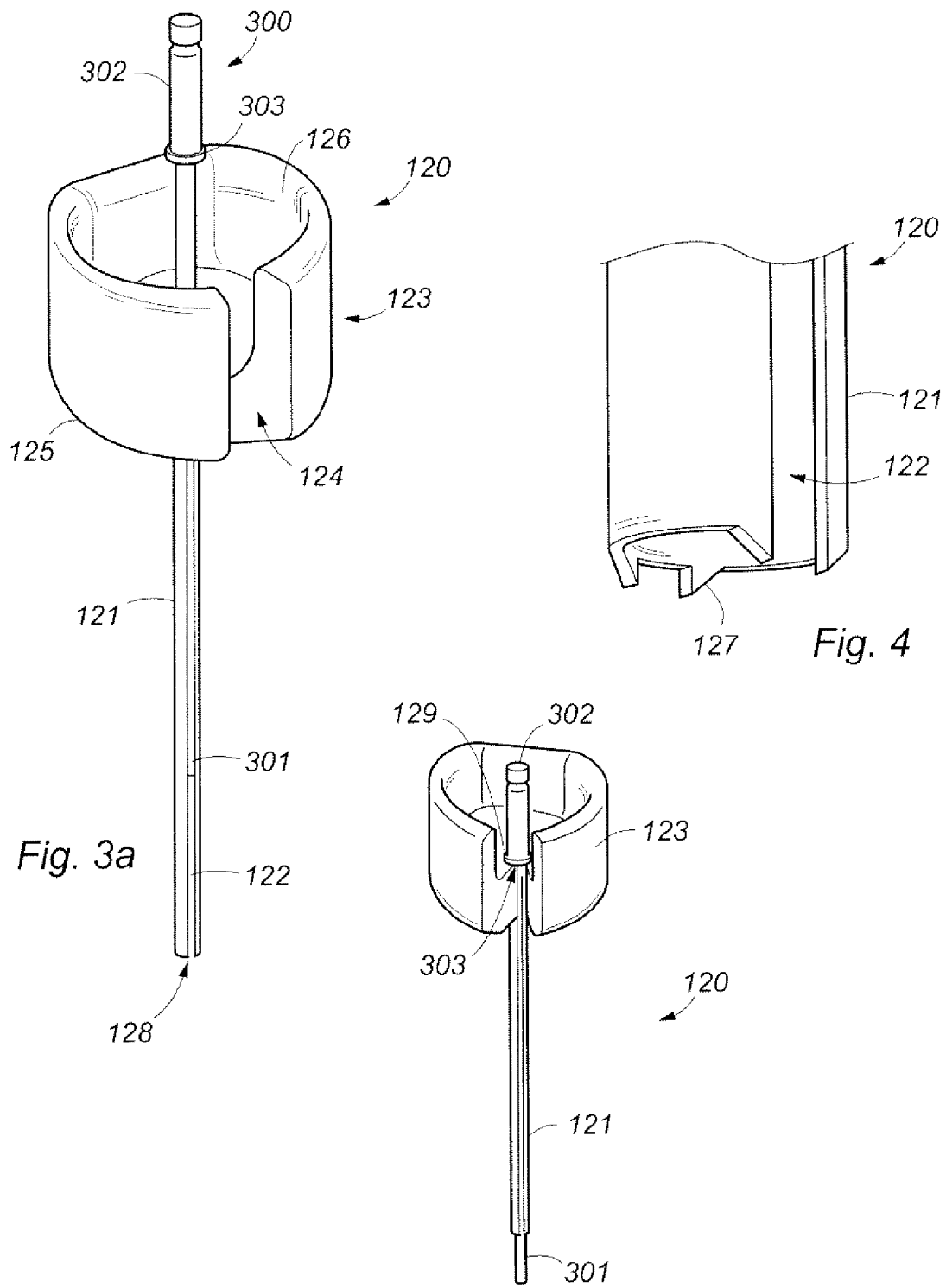

INSTRUMENT FOR IMPLANTING A SENSOR

This invention relates to an instrument for implanting a sensor in a body part, and in particular to an instrument for implanting a sensor that has at least one cord extending therefrom which is connected to an external device.

Sensors can be implanted into a body part of a patient for applications such as measuring temperature, and analysing material composition. In many surgical procedures, it can be useful to use a sensor as a marker whose location can be determined and tracked by a tracking system. A tracking sensor of this kind can be used in a catheter (or catheter guide wire) while it is navigated through a patient's vessels. It can be used in orthopaedic procedures in which the position of instruments and implants relative to a patient's bone tissue is monitored.

Implantable sensors can have a cord extending from the sensor. The cord can have a mechanical function, for example for use as a suture, or to be gripped when the sensor is to be removed from the body. It can be particularly preferred for the cord to contain conductors by which signals can be transmitted to an external device. for example, a signal can be transmitted to a data processor through the conductors. Alternatively, the signal can be transmitted through the conductors to a transmitter by which the signals are then transmitted wirelessly to a receiver.

When the sensor is used as a marker, a system in which the sensor is incorporated can be used to track the location of the sensor. This can be achieved using electromagnetic techniques. U.S. Pat. Nos. 5,391,199 and 5,443,489 provides details of systems which are applicable to the present invention, in which the coordinates of an intrabody probe are determined using one or more field transducers, such as a Hall effect device, coils, or other antennae carried on the probe. Such systems are used for generating location information regarding a medical probe or catheter. A sensor, such as a coil, is placed in the probe and generates signals in response to externally-applied magnetic fields. The magnetic fields are generated by magnetic field transducers, such as radiator coils, fixed to an external reference frame in known, mutually-spaced locations. Systems which are concerned with tracking a sensor in a three-dimensional space are also disclosed in WO-96/05768, U.S. Pat. No. 6,690,963 and US-A-2002/0065455. Subject matter that is disclosed in the specifications of the patents and patent applications referred to in this paragraph is incorporated in this specification for all purposes by these references.

A U.S. patent application filed with the present application on Feb. 22, 2005, with the title "Reference Pad for Position Sensing", and having U.S. patent application Ser. No. 11/063,094, discloses magnetic tracking systems for use in tracking the positions of objects related to a medical procedure, such as medical tools and intrabody devices. Subject matter that is disclosed in the specification of that application is incorporated in this specification for all purposes by this reference. The system comprises one or more location pads attached to the body and one or more position transducers that are inserted into the body. In some embodiments, the location pads transmit magnetic fields, which are received by the transducers. In other embodiments, the transducers inside the body transmit magnetic fields, which are received by the location pads. In both cases, the received field amplitudes are used in determining the coordinates of the transducers in the body relative to one or more of the location pads.

Typically, each location pad is attached to the body surface close to the area in which the position transducer is located. As a result, accurate coordinates may be determined while transmitting relatively weak magnetic fields, and interference of metal objects with the tracking system is reduced. There is no limitation on movement of the patient's body during the medical procedure, since the location pad moves together with the body.

In some embodiments of the present invention, one of the position transducers is fixed to a structure inside the body, and another position transducer is attached to a surgical tool. Both the fixed transducer and the tool transducer transmit or receive magnetic fields to or from the same location pad. By processing the received field amplitudes, the coordinates of the tool and the fixed transducer relative to the location pad are determined, and thus the coordinates of the tool relative to the fixed transducer is known. The relative coordinates may be used to guide a medical practitioner in manipulating the tool to perform a medical procedure on the body structure to which the position transducer inside the body is fixed.

In some embodiments, these systems are used in orthopaedic procedures, such as implantation of implants such as screws, nails, rods or prosthetic joints. For this purpose, wireless or wired magnetic position transducers may be inserted into the patient's bone, into prosthetic implants and into tools used during surgery. The tracking system determines the coordinates of the transducers, and thus enables the surgeon to visualize the locations and orientations of these elements while reducing or eliminating the need for intraoperative X-ray imaging. Implanted position transducers may also be used in post-operative follow-up. In other embodiments, body-surface location pads are used in conjunction with position transducers in body structures and devices used in other medical procedures, such as endoscopy and cardiovascular catheterization.

When implanting a sensor which is connected to an external device by means of a wire, it is important that during implantation of the sensor, the wire and the connections between the wire and the sensor and the external device are not damaged or compromised.

The present invention provides an instrument for implanting an sensor which is connected to an external device via a wire which comprises first and second sheaths having slots formed in them along their lengths to aid insertion of the sensor and provide for subsequent removal of the instrument from the sensor.

According to a first aspect of the invention, there is provided an instrument for implanting a sensor in a body part, in which the sensor has at least one cord extending therefrom which is connected to an external device, the instrument comprising: a guide sheath for defining a path to the surface of the body part through overlaying soft tissue, the sheath having a bore extending along its length between first and second open ends through which the tool can pass and a slot that extends along its length between its first and second open ends; and a delivery sheath for inserting the sensor in the hole, the delivery sheath having a bore extending along its length between a first open end at which the sensor can be mounted and a second end, with the cord extending from the sensor along the bore, in which the sheath has a slot that extends along its length between its first and second end, and wherein the delivery sheath can be received within the guide sheath by sliding the delivery sheath within the bore of the guide sheath; wherein the slots of the guide and delivery sheaths can be aligned to allow the cord to be removed from the bores other than at the ends of the bores.

The instrument of the invention has the advantage that an implantable sensor which includes a cord can be implanted in a patient's body and fixed in place, while the guide and delivery sheaths are in place in contact with the patient's body. This is not possible without the aligned slots in the sheaths through which the cord can be removed from the instrument. In particular, the provision of slots in the guide and delivery sheaths which allow the wire to be removed from the bore other than at the end of the bores provides the ability to remove the sensor, any external device and a wire extending between them from the instrument without needing to disconnect the wire from one of the sensor or external device. This is because, once the sensor has been implanted in the body part, the wire which extends through the bores of the sheaths can be freed from the sheaths by sliding it out through the slots. It has been found that this gives rise to a significant increase in the ease by which the sensor can be implanted as the surgeon no longer needs to subsequently connect the wire to one of the sensor or external device once the sensor has been implanted. This has been found to in turn dramatically decrease the time it takes to implant the sensor and hence reduce the duration of the medical procedure.

The instrument of the present invention provides a guide sheath which can be pushed through the overlaying tissue first, and then the sensor can be passed through the guide sheath. Therefore, the sensor and wire can be protected from the overlaying tissue by the guide sheath. The instrument of the present invention can therefore help prevent damage to the sensor and wire. Also, the overlaying tissue surrounding the guide sheath is protected from the sensor and the delivery sheath during the step of implanting the sensor in the body part. Therefore, the instrument of the present can therefore help reduce damage to the overlaying tissue.

The provision of separate guide sheaths and delivery sheaths gives rise to the advantage that the delivery sheath is also protected from tissue surrounding the guide sheath. This can be advantageous as a clean path through the guide sheath is provided for the sensor and delivery sheath thereby helping to prevent damage to the sensor and/or the delivery sheath.

When the sensor is to be implanted in a pre-formed hole in a body part, the guide sheath can be used to guide a tool into the body part in order to create the hole. For example, when the hole is to be created by a drill bit, the drill bit can extend through the bore in the guide sheath and can protrude from the end of the guide sheath in order to extend into the body part. Therefore, the guide sheath can be used to determine the axis of the hole which is to be created by the tool. This is particularly advantageous, because once the hole has been created, the tool can be removed from the guide sheath and the delivery sheath inserted into the guide sheath to implant the sensor in the hole. As the guide sheath can be retained in its position subsequent to the hole forming, the guide sheath can help ensure proper implantation of the sensor in the hole. This is because, the axes of the hole and the guide sheath will be aligned and therefore the sensor will be guided cleanly into the hole by the guide sleeve. The use of a guide sleeve which is retained subsequent to the hole forming step means that there is no need for the surgeon to locate the hole. Instead, the surgeon can push the sensor through the guide sheath using the delivery sheath in the knowledge that the guide sheath will lead the sensor to the hole.

The provision of slots in the guide and delivery sheaths allow the wire to be removed from the bore other than at the end of the bores. This provides the ability to remove the sensor, external device and the wire extending between them from the instrument without needing to disconnect the wire from one of the sensor or external device. This is because, once the sensor has been implanted in the body part, the wire which extends through the bores of the sheaths can be freed from the sheaths by sliding it out through the slots. It has been found that this gives rise to a significant increase in the ease by which the sensor can be implanted as the surgeon no longer needs to subsequently connect the wire to one of the sensor or external device once the sensor has been implanted. This has been found to in turn significantly decrease the time it takes to implant the sensor and hence reduce the duration of the medical procedure.

Preferably, the delivery sheath is open at its second end so that when the sensor is loaded in the delivery sheath the wire can extend through the bore and out of the second open end. This can be advantageous as it can ensure that the wire is fully received in the bore during implantation of the sensor. This can help prevent damage to the wire during implantation of the sensor.

The width of the slot in the guide sheath, in a direction perpendicular to the axis of the guide sheath is larger than the diameter of the cable, in order to allow passage of the cable through the slot. Preferably, the width of the slot is only slightly larger than the diameter of the cable so as to prevent the slot from easily falling out of the guide sheath through the slot during implantation of the sensor. Preferably, the ratio of the width of the slot to the width of the cable is no more than 1.5, more preferably no more than 1.4, especially preferably no more than 1.3, for example no more than 1.1.

The width of the slot in the delivery sheath, in a direction perpendicular to the axis of the delivery sheath is larger than the diameter of the cable, in order to allow passage of the cable through the slot. Preferably, the width of the slot is only slightly larger than the diameter of the cable so as to prevent the slot from easily falling out of the guide sheath through the slot during implantation of the sensor. Preferably, the ratio of the width of the slot to the width of the cable is no more than 1.5, more preferably no more than 1.4, especially preferably no more than 1.3, for example no more than 1.1.

Preferably, the guide sheath has teeth at its first end arranged to engage the surface of the body part. This can be particularly advantageous because it can help prevent movement of the first end of the guide sheath along the surface of the body part during implantation of the sensor. In particular, when the sensor requires a hole to be pre-formed in the body part, the teeth can help prevent the first end moving between the step of forming the hole and implanting the sheath. Therefore, the provision of teeth at the first end of the guide sheath can increase the ease by which the sensor can be implanted.

Preferably, the guide sheath has a handle located at its second end to facilitate holding of the guide sheath during use. This can be advantageous as it can help ensure that the surgeon can keep the guide sheath stable during implantation of the sensor. Therefore, the provision of a handle on the guide sheath can help prevent movement of the guide sheath during the implantation of the sensor.

Preferably the handle of the guide sheath extends around the circumference of the guide sheath and in which the handle has a slot extending there through, the slot being aligned with the slot in the guide sheath, so as to allow the wire to slide out of the guide sheath. It is particularly advantageous to provide a handle that extends around the circumference of the guide sheath as this allows a surgeon to clasp the handle and hence increase the ease by which the surgeon can hold the guide sheath stable during implantation of the sensor. The provision of the slot in the handle ensures that the sensor, external device and wire extending there between can easily be removed from within the bore of the guide sheath as explained above.

Preferably, the delivery sheath has a handle located at its second end to facilitate holding of the delivery sheath during use.

Preferably, the handle extends around the circumference of the delivery sheath, and in which the handle has a slot extending there through, the slot being aligned with the slot in the delivery sheath, so as to allow the wire to slide out of the delivery sheath.

The provision of the slot in one or each handle ensures that the sensor, external device and wire extending there between can easily be removed from within the bore of the guide sheath, without the need to disconnect the wire from the sensor and/or external device. As explained above, there are many advantages associated with removing the need to disconnect the wire from the sensor and/or external device during implantation of the sensor. It also means that the sensor, external device and wire can be supplied with all connections between them already made.

Preferably, the handle of the guide sheath and handle of the delivery sheath are shaped so that the delivery sheath can only be received in the guide sheath when the slots are aligned. This is particularly advantageous as it reduces the need for the surgeon to align the slots manually during implantation of the sensor. For example, one of the handles can have a recess formed in it in the surface which faces the other handle, and the other handle can have a spigot which is shaped so that it can be received in the recess. The shape of the recess and the spigot can be such that the handles will only fit together when the recess and spigot are appropriately aligned. Preferably, there is only one orientation of the handles in which they can fit together.

Preferably the handles of the guide and the delivery sheath are configured to facilitate self-alignment of the sheath. For example, when the handles provide a matching spigot and recess combination, the facing edges of the spigot and the recess can be rounded so that the spigot is led into the recess. This can be advantageous as the surgeon can simply bring the handles of the guide and delivery sheaths together and press them together and in doing so the sheaths rotate relative to one other until the slots thereof are aligned. Again, this increases the ease of assembly of the instrument and thereby increases the ease by which the sensor is implanted into the body part.

Preferably, one of the handle of the guide sheath and the handle of the delivery sheath includes a non-circular socket and the other includes a spigot configured to be received in the socket, the spigot and socket being contoured to facilitate self-alignment of the sheaths for insertion of the delivery sheath within the guide sheath. Preferably, the non-circular socket and corresponding spigot are shaped so that the spigot can only be received in the socket in one angular orientation. Therefore, this ensures that the slots of the guide and delivery sheaths and of the handles will be aligned when the spigot is properly received within the socket.

The handle of the guide sheath can be formed to be part of the guide sheath. For example, the handle and guide sheath can be moulded as one unit.

Preferably, the handle of the delivery sheath can be formed to be part of the delivery sheath. For example, the handle and delivery sheath can be moulded as one unit.

Preferably, the handle for either or each of the sheaths is formed separately from the sheath, and subsequently fastened to the sheath. This can ease manufacture of the handle and the sheath. The handle of the sheath can be formed by moulding, for example injection moulding. Preferably, the handle is permanently fastened to the sheath. For example, the handle can be fastened to the sheath by bonding, including welding, or using an adhesive. The connection between the handle and the sheath should be capable of withstanding techniques used for sterilisation, for example involving exposure to radiation, or to high temperatures and pressures. Suitable materials will be known to the skilled reader.

Preferably, the external device can be temporarily attached to the second end of the delivery sheath during implantation of the sensor. This can aid implantation of the sensor as the sensor, external device and wire can be manipulated as one unit by manipulating the delivery sheath. Preferably, the handle of the delivery sheath includes a socket formed in it which is shaped and sized to receive the external device. The provision of such a socket in the handle provides a simple way of temporarily attaching the external device to the delivery sheath. This is because the external device can be placed within the socket. The walls of the socket can ensure that the external device does not move within the socket and fall out of the handle during implantation. Once the sensor has been implanted, the external device can be removed from the socket by pulling it out along the axis of the socket.

In another aspect, the invention provides an assembly comprising an instrument according to the invention, and a sensor mounted at the first end of the delivery sheath.

In a further aspect, the invention provides a method of implanting a sensor in a body part, in which the sensor has at least one cord extending therefrom for connection to a device external to the bone, the method comprising: inserting a guide sheath through tissue surrounding the body until a first open end of the sheath contacts the desired site on the bone, the guide sheath having a bore extending along its length between the first open end and a second open end; mounting the sensor at a first open end of a delivery sheath, the delivery sheath having a bore extending along its length between the first open end and a second end, so that the sensor is located at the first end of the delivery sheath and the cord extends from the sensor along the bore; and sliding the delivery sheath through the guide sheath until the sensor is located at the site at which the sensor is to be implanted; implanting the sensor in the body part; pulling the guide and delivery sheaths away from the sensor and out of the tissue so as to leave the sensor in the body part; and feeding the cord through the slots of the delivery and guide sheaths to remove the sensor from the bores of the sheaths.

It can be important in patients with a thick layer of tissue overlying the part in which the sensor is implanted to ensure that there is an adequate length of the cord within that layer of tissue to accommodate relative lateral movement between the part and the skin on which the external device is placed. It can therefore be preferred for the method of implanting the sensor to include a step of manipulating soft tissue which overlies the implanted sensor prior to any subsequent step of fastening or otherwise managing loose cord which protrudes from the tissue.

Accordingly, in yet another aspect, the invention provides a method of implanting a sensor in a body part, in which the sensor has a cord extending from it and in which the body part has a layer of overlying soft tissue, which includes the steps after implanting the sensor in the body part of manipulating the soft tissue to cause relative transverse movement between skin on the soft tissue and the body part, and then tidying excess cord which protrudes from the tissue to prevent snagging during subsequent surgical procedure steps.

Preferably, the sensor has an associated external device to which it is connected by means of the cord. Preferably, the method includes the step of fastening the external device to the patient's skin in the vicinity of the location of the implanted sensor. Preferably, the method includes the step of fastening loose wire which extends between the external device and the point of entry to the patient's tissue with adhesive tape.

The guide sheath and the delivery sheath will generally be made from metallic materials which are conventionally used in the manufacture of surgical instruments. Certain stainless steels can be particularly preferred.

Preferably, the sensor comprises a jacket part and a sensor part. Preferably the jacket part has a line of weakness extending along its length which facilitates transverse compression of the jacket when the sensor is implanted in a hole, especially in a hole in a bone. A cord can be attached to the sensor to apply force to the sensor to remove it from the hole in the bone. Preferably, the sensor part is fastened to the jacket at or towards a first end of the jacket, so that the sensor part is at least partially isolated from compressive forces applied to the sensor which cause the side wall of the jacket to deform inwardly. Details of a sensor which comprises a jacket part and a sensor part are disclosed in UK and U.S. patent applications filed with the present application with the title Implantable Sensor. Subject matter that is disclosed in the specification of that application is incorporated in this specification for all purposes by this reference.

The cord which extends from the sensor can include conductors by which signals can be transmitted to or from the sensor or both, or by which power can be supplied to the sensor. The cord can be arranged for application of a load to the sensor, for example to remove the sensor from a hole in a bone. The cord can therefore include load bearing components. Suitable polymeric materials for such load bearing components include aramids such as sold under the trade mark Kevlar. Preferably, the cord includes conductors and load bearing components.

Embodiments of the present invention will now be described by way of example only with reference to the accompanying drawings in which:

FIG. 3a shows a perspective view of the delivery sheath of the instrument shown in FIG. 2 with a drill bit partially inserted therethrough;

FIG. 3b shows the delivery sheath shown in FIG. 3a with the drill bit fully received within the guide sheath;

FIG. 4 is an exploded perspective view of the end of the guide sheath shown in FIG. 3a;

Figure 1:
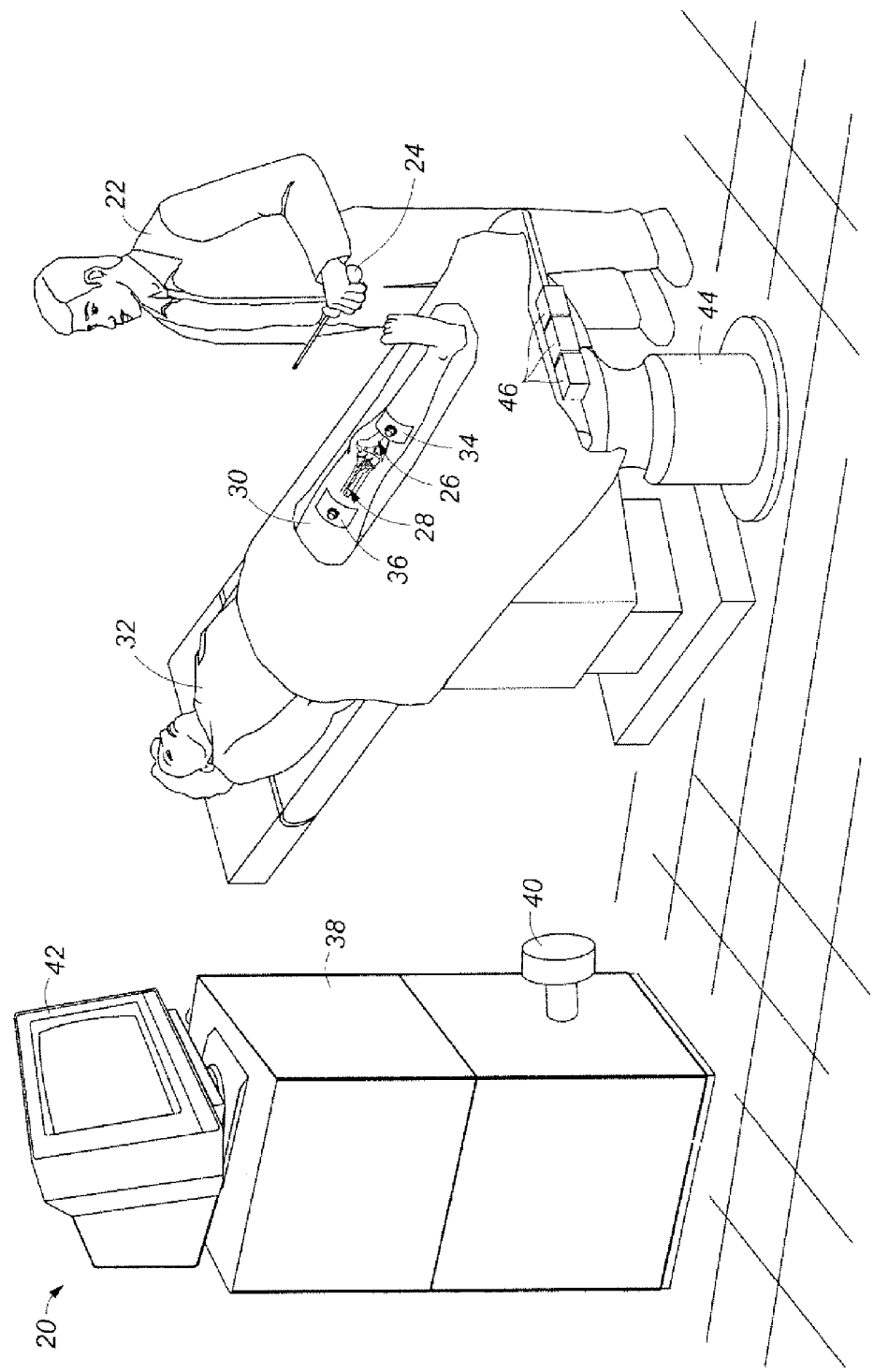
FIG. 1 is a schematic, pictorial illustration of a magnetic tracking system used in surgery, in accordance with an embodiment of the present invention.

Referring to the drawings, FIG. 1 is a schematic, pictorial illustration of a magnetic tracking system 20 for use in surgery, in accordance with an embodiment of the present invention. In the pictured embodiment, a surgeon 22 is performing a procedure that involves manoeuvring a tool 24 to positions in contact with, or relative to, implantable devices or probes 26, 28, hereinafter referred to as implants 26, 28. In the example of FIG. 1, implants 26, 28 have been introduced into the body at a surgical site, which is located in a leg 30 of a patient 32. In this example, implants 26, 28 have been introduced into the patient's tibia and femur near the knee, for use in guiding the surgeon in performing a procedure on the knee joint using tool 24.

Both the tool 24 and the implants 26, 28 contain miniature, wireless position transducers, which are described in detail below. In this embodiment, the transducers are wireless, but the transducers may alternatively have wired connections for electrical power and communications. Each transducer may be designed either to transmit or receive magnetic fields. The fields are used in generating position signals indicative of the transducer's location and orientation coordinates, as described below. Tracking system 20 thus enables surgeon 22 to monitor the position of tool 24 relative to implants 26, 28 throughout a working volume that comprises the space around and including the surgical site. Additional medical devices and tools with position transducers similar to those of implants 26, 28 may also be used at additional locations in the area of the surgical site. For example, the use of such position transducers in a hip implant is disclosed in US-A-2003/0120150. Subject matter that is disclosed in the specification of that application is incorporated in this specification for all purposes by this reference.

Alternatively, although the embodiment shown in the figures relates to orthopaedic applications, the principles of the present invention may similarly be applied in other types of medical applications. For example, location pads 34, 36 may be used in determining the coordinates of position transducers in invasive probes, such as catheters and endoscopes, which are inserted into the cardiovascular system and other organs of the body.

The coordinates of the transducers in tool 24 and implants 26, 28 are determined relative to location pads 34, 36, which are fixed to the body. The pads may conveniently be glued or strapped on to the body surface, or held against the skin by some other means. In the example shown in FIG. 1, these pads are placed on the patient's calf and thigh, in proximity to implants 26, 28. Alternatively, the location pads may be held away from the skin by support structures that are fixed to the body, so that the pads move with the body part to which they are in proximity. Location pads 34, 36 comprise magnetic field transducers, such as coils, which are used to transmit or receive magnetic fields. In other words, if the transducers in implants 26, 28 and in tool 24 are configured to receive magnetic fields, then location pads 34, 36 are configured as field generators. Alternatively, the location pads may be configured to receive fields generated by the position transducers in the implants and the tool. For the sake of simplicity in the description that follows, it is assumed that location pads 34, 36 transmit the magnetic fields, which are received by the transducers in implants 26, 28 and in tool 24. The roles of transmitter and receiver may be reversed in a straightforward manner.

The field generator coils in pads 34, 36 generate electromagnetic fields at different, respective sets of frequencies $\{\omega 1\}$ and $\{\omega 2\}$. Typically, the sets comprise frequencies in the approximate range of 100 Hz to 30 kHz, although higher and lower frequencies may also be used. The sets of frequencies at which the coils radiate are set by a computer 38, which serves as the system controller for system 20. For the purposes of system 20, pads 34, 36 are placed in close proximity to the surgical site so that minimal energy is needed to generate the magnetic field. The pads are typically positioned such that the working volume of the tracking system includes the entire area in which the surgeon is operating. Furthermore, pads 34, 36 are positioned so as not to impede access to the surgical site.

At any instant in time, the applied magnetic fields induce currents in coils contained in the transducers of tool 24 and of implants 26, 28. The induced currents comprise components at the specific frequencies in sets $\{\omega 1\}$ and $\{\omega 2\}$. The respective amplitudes of these currents (or alternatively, of time-varying voltages that may be measured across the transducer coils) are dependent on the location and orientation of the position transducer relative to the locations and orientations of the field generator coils. In response to the induced currents or voltages, signal processing and transmitter circuits in each position transducer generate and transmit position signals that are indicative of the location and orientation of the transducer.

These position signals are received by a wireless control unit 40, which is coupled to computer 38. Alternatively, the transducers of tool 24 and of implants 26, 28 may be connected by wire directly to computer 38. The computer processes the received signals in order to calculate the relative location and orientation coordinates of tool 24 and of implants 26, 28. Below, the relative location and/or orientation of one object to another, determined in any or all of six dimensions, is referred to as the relative disposition of the two objects. Of the six dimensions, three dimensions represent the X, Y, and Z coordinates of one object relative to the other. Three additional dimensions represent the angular orientation of one object relative to the other. Disposition in one dimension, for example, may mean simply the distance between the origins of the two objects.

The disposition of the tool relative to each of the implants is calculated based on the magnetic field that is generated by the location pad on the limb in which the implant is located. In other words, in the example shown in FIG. 1, the disposition of the tool relative to implant 26 is calculated based on the field generated by location pad 34, while the disposition of the tool relative to implant 28 is calculated based on the field generated by location pad 36. Consequently, the disposition of the tool relative to each of the implants (and hence of the bones in which the implants are located) can be determined accurately notwithstanding motion of leg 30.

Optionally, one of the location pads may also comprise a position transducer that receives the magnetic field generated by the other location pad. The signals received by this transducer may then be used by computer 38 in registering the separate, "floating" coordinate systems of the two location pads. The registration may be updated whenever leg 30 is moved. In this case, determination of the coordinates of tool 24 in the frame of reference of either of location pads 34, 36 is sufficient to determine the disposition of the tool relative to both of implants 26, 28.

In embodiments in which the coordinate systems of multiple location pads are mutually registered, computer 38 determines the coordinates of tool 24 using the location pad that gives the most accurate position signal. Typically, the coordinates of the tool are determined based on the magnetic field that the tool transducer receives with the least noise or interference. As the tool moves through the working volume, a magnetic field signal from a first pad may initially provide the greatest accuracy and is therefore used to determine the relative disposition of the tool and the implants. Subsequently, the field from a second pad may generate a more accurate position signal, and the tracking process is "handed-off", such that the disposition coordinates are now determined based on the field from the second pad.

The coordinates are used by the computer in driving a display 42, which shows the dispositions of the tool, screw and other elements (such as prosthetic implants) to which position transducers have been fixed.

Whereas system 20 is shown as comprising a specific configuration of implants, tools, and body surface pads, in other embodiments of the present invention, different numbers, types and configurations of devices may used.

In other embodiments of the invention, as noted above, the generation and reception of the magnetic fields are reversed such that the coils in the implants and in the tool generate the position-responsive magnetic fields, and the body surface pads receive the fields. The relative disposition of the tool and either of the implants is determined as above, by comparing the position signals induced in pads 34, 36 by the fields radiated from the tool and the implant. In further embodiments, any or all of the set of tools, implants, and pads may comprise transducers configured to receive and to generate magnetic fields, such that there is flexibility in selecting the coordinate system and the floating origin.

Additionally or alternatively, a field transducer 46 may be attached to a fixed frame of reference, such as an operating table 44 on which patient 32 is lying, and used as a fixed coordinate reference. Magnetic fields transmitted between fixed field transducer 46 and the location pads on the patient's body may be used to register the floating origin of the location pad coordinates with the fixed frame of reference.

When a metal or other magnetically-responsive article is brought into the vicinity of an object being tracked, such as implant 26 or tool 24, the magnetic fields in this vicinity are distorted. In the surgical environment shown in FIG. 1, for example, there can be a substantial amount of conductive and permeable material, including basic and ancillary equipment (operating tables, carts, movable lamps, etc.), as well as invasive surgery apparatus (scalpels, scissors, etc., including tool 24 itself). The magnetic fields produced by the field generator coils may generate eddy currents in such articles, and the eddy currents then cause a parasitic magnetic field to be radiated. Such parasitic fields and other types of distortion can lead to errors in determining the position of the object being tracked.

In order to alleviate this problem, the elements of tracking system 20 and other articles used in the vicinity of the tracking system are typically made of non-metallic materials when possible, or of metallic materials with low permeability and conductivity. In addition, computer 38 may be programmed to detect and compensate for the effects of metal objects in the vicinity of the surgical site. Suitable methods for such detection and compensation are disclosed in U.S. Pat. Nos. 6,147,480, 6,373,240, US-A-2004/0240240 and US-A-2005/0024043. Subject matter that is disclosed in the specification of those patents and patent applications is incorporated in this specification for all purposes by these references.

Figure 2:
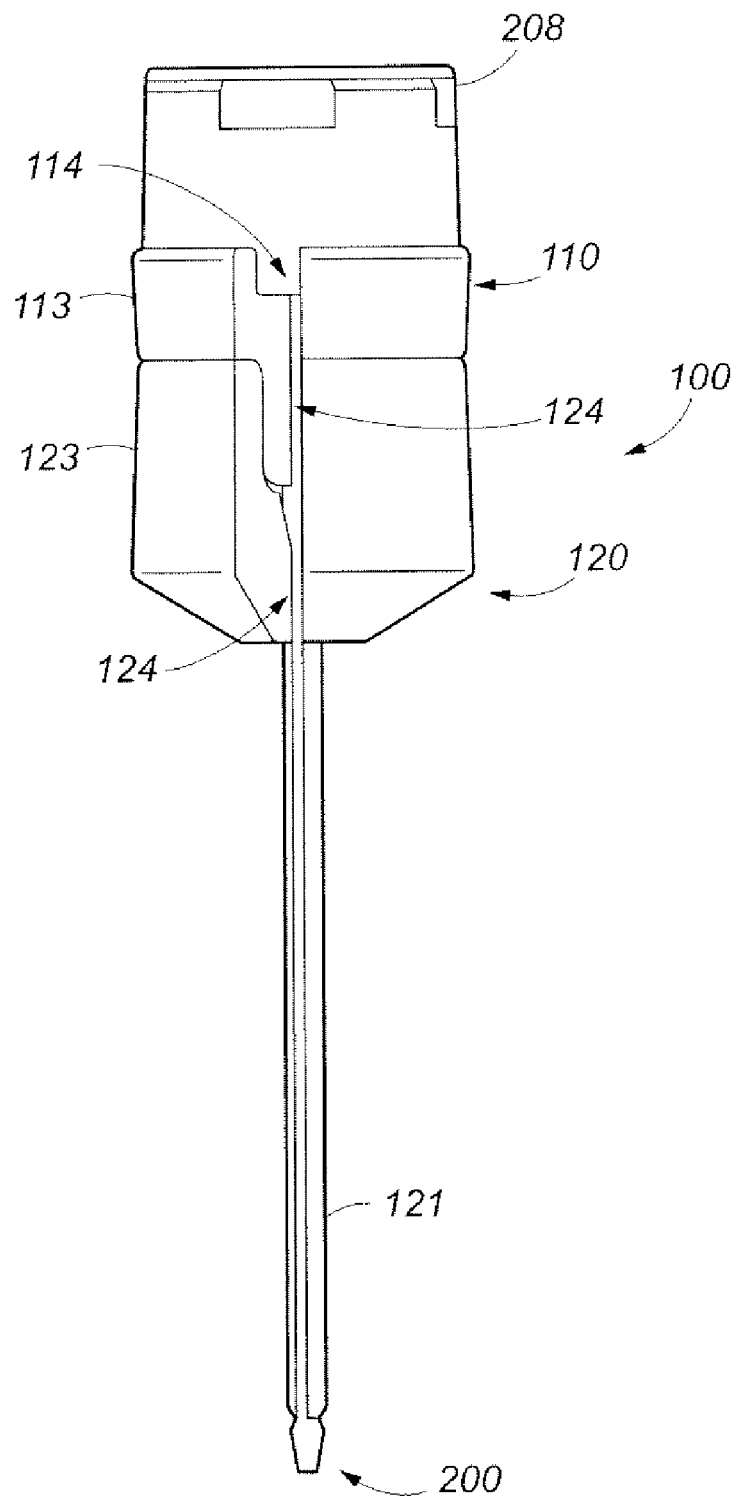
FIG. 2 shows a side view of an instrument according to the invention assembled with a sensor.
Figure 5:
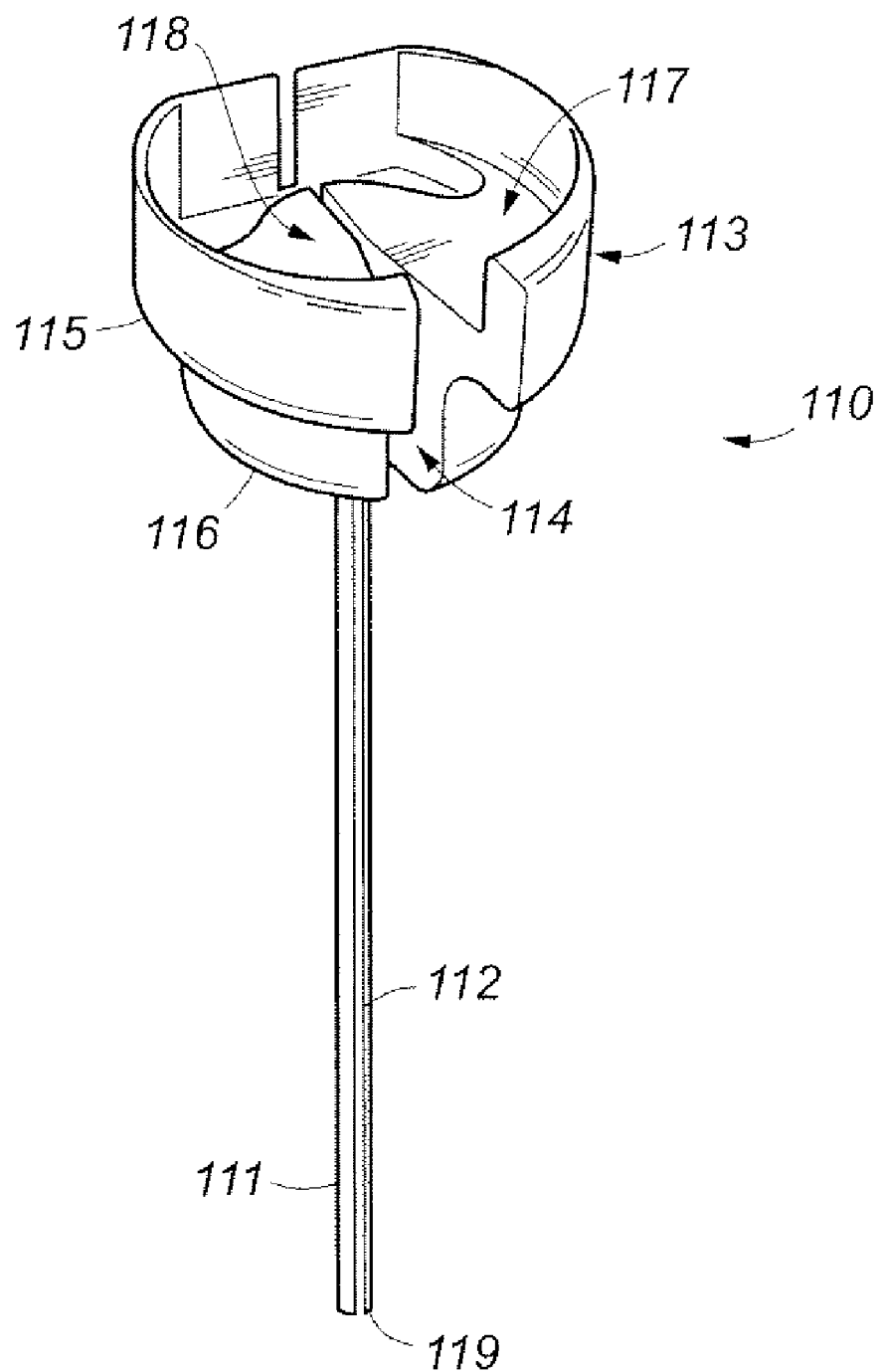
FIG. 5 is a perspective view of the delivery sheath of the instrument shown in FIG. 2.

As shown in FIG. 2, there is shown an illustration of an instrument 100 according to the invention in which the sensor 200 has been mounted in the delivery sheath 110 of the instrument. The instrument 100 generally comprises a delivery sheath 110 and a guide sheath 120.

For illustrative purposes only, the sensor described hereinafter is a sensor that can be tracked by a tracking system in order to track the location of the body part in which the sensor is implanted. Also, for illustrative purposes only, the instrument as described hereinafter is used to implant the sensor into a bone. However, as will be understood and as described above, the invention can be used with other sensors used for different purposes, and the instrument can be used to implant the sensor into body parts other than a bone. Further, the sensor described is of the press-fit type which requires a hole to be preformed in the bone for it be implanted in the bone. However, it will be appreciated that sensors which do not require a hole to be pre-formed in the bone can be implanted using the instrument of the present invention.

Figure 9:
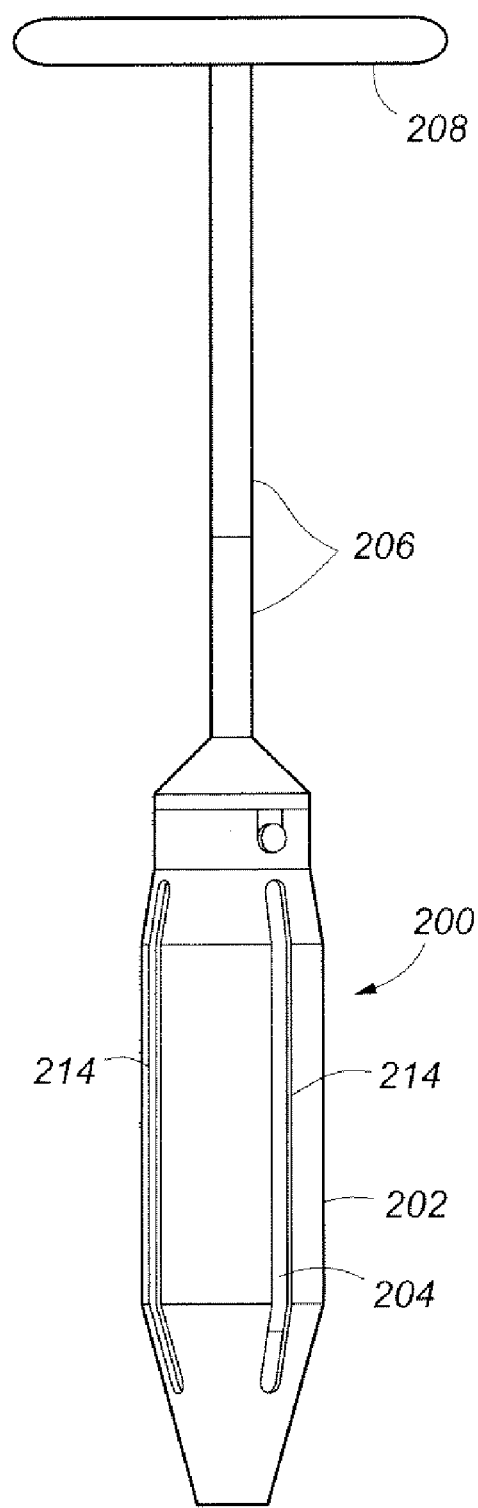
FIG. 9 shows a schematic side view of a sensor that can be implanted into a body part using the instrument shown in FIGS. 2 to 7 and a schematic illustration of an external device to which the sensor is connected and a computer to which the external device is connected.

With reference to FIG. 9, there is shown a schematic illustration of the implantable sensor 200 which can be implanted by the instrument 100. The sensor has an elongate configuration and includes an external jacket 202 which encloses a sensor part 204. The sensor has a cable 206 extending from a first end which is connected to an external device 208, hereinafter referred to as a "reference pad".

The jacket 202 has slits 214 which facilitates radial compression of the jacket so as to allow the sensor to be implanted into a hole in a bone which has a diameter smaller than that of the jacket in an uncompressed state. The jacket 202 is resiliently deformable, so that when the sensor is implanted in the hole in a bone, the elastic property of the material of the jacket urges the walls of the body of the jacket against the inner walls of the hole so as to provide a retaining force helping to keep the sensor in place in the hole.

In the embodiment shown, the reference pad 208 is configured to generate a magnetic field. The sensor 200 is responsive to the magnetic field, and can generate and transmit a position signal to the reference pad via the cable 206, wherein the position signal indicates the location of the sensor relative to the reference pad 208. The reference pad 208 is able to communicate with an external computing device (not shown) in order to provide the position signals to the computing device. The reference pad 208 can be connected to the computing device by a wireless connection, or by a physical wired connection. As will be understood, when the reference pad 208 physically connected to the computing device, power to the reference pad and/or the sensor 200 can be provided by the cable connecting the reference pad and the computing device. Upon receiving the position signals, the computing device is able to determine the position of the sensor relative to the reference pad.

With reference to FIGS. 2, 3a, 3b, 4, 6 and 7, the guide sheath will be described in more detail. Guide sheath 120 comprises a tubular sheath 121 having a first end 128 which during use abuts the surface of the bone, and a second end 129 distal to the first end. The tubular sheath 121 has a bore extending through it, along its length, between the first 128 and second 129 ends. The tubular sheath 121 has a slot 122 formed in it that extends along its length, between the first 128 and second 129 ends, so as to provide a path between the bore of the tubular sheath and the exterior of the tubular sheath.

The tubular sheath 121 has at its first end 128 a plurality of teeth 127 extending axially therefrom for engagement with the bone at the site in which the sensor 200 is to be inserted. The teeth 127 are mutually spaced around the first end 128 of the tubular sheath 121.

The guide sheath 120 includes a substantially annular handle 123 to facilitate holding of the guide sheath by a surgeon. The handle 123 extends around the circumference of the tubular sheath 121 at the second end 129. The handle 123 has a slot 124 extending through its substantially annular side wall 125, the slot of the handle being aligned with the slot 122 of the tubular sheath 121 so as to provide a path between the exterior of the side wall 125 and the bore extending through the tubular sheath 121.

The substantially annular side wall 125 of the handle 123 extends axially away from the first end 128 of the tubular sheath and as such defines a socket 126 in the handle 123 for receiving a spigot 116 of the handle 113 of the delivery sheath 110 described hereinafter. The cross-sectional shape of the socket 126 taken in a plane perpendicular to the longitudinal axis of the tubular sheath 121 is generally that of a circle having a flat side. As described hereinafter, this ensures that the spigot 116 of the delivery sheath 110 can only be received in the socket 126 in one angular orientation.

The tubular sheath 121 is configured to be able to receive a drill bit 300 through its bore. As shown in FIGS. 3a and 3b, the drill bit 300 comprises a cutting end 301 at a first end of the drill bit for cutting a hole into a bone, and a second end 302 distal to the cutting end which is configured to facilitate attachment of the drill bit to a tool (not shown) for imparting a rotational force on the drill bit. An annular flange 303 is provided towards the second end of the drill bit. The diameter of the annular flange 303 is greater than the diameter of the bore within the tubular sheath 121, to limit the extend by which the drill bit 300 can slide through the tubular sheath 121. The flange 303 thereby controls the extent by which the drill bits 300 can extend through the tubular sheath and accordingly can control the depth of the hole created by the drill bit 300.

With reference to FIGS. 2, 5, 6 and 7, the delivery sheath 110 will now be described in more detail. The delivery sheath 110 comprises a tubular sheath 111 that has a first end 119 which during use is proximal the surface of the bone, and a second end 130 distal to the first end. The tubular sheath 111 has a bore extending through it, along its length, between the first 119 and second 130 ends. The tubular sheath 111 has a slot 112 formed in it that extends along its length, between the first 119 and second 130 ends, so as to provide a path between the bore of the tubular sheath and the exterior of the tubular sheath. The tubular sheath 111 of the delivery sheath 110 is shaped and sized so as to be able to slide within the bore of the tubular sheath 121 of the guide sheath 120, and described in more detail hereinafter.

The delivery sheath 110 includes a substantially annular handle 113 to facilitate holding of the delivery sheath by a surgeon. The handle 113 extends around the circumference of the tubular sheath 111 at its second end 130. The handle 113 has a slot 114 extending through its substantially annular side wall 115, the slot of the handle being aligned with the slot 112 of the tubular sheath 111 so to provide a path between the bore of the tubular sheath 111 and the exterior of the handle 113.

The handle 113 includes a spigot 116 that extends axially towards the first end 119 of the tubular sheath 111. The socket 126 of the handle 123 of the guide sheath 120, and the spigot 116 are shaped and sized so as to enable the spigot to be received in the socket.

The substantially annular side wall 115 extends away from the first end 119 of the tubular sheath 111 and defines a socket 117 in the handle 113 for receiving an external device such as the reference pad 208 which is connected to the sensor 200 via cable 206 described above with reference to FIG. 9.

Figure 6:
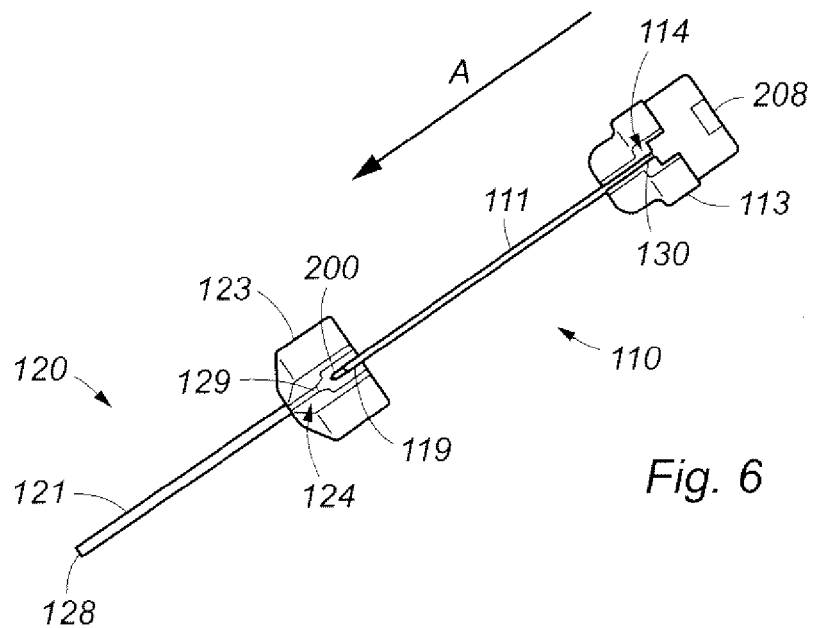
FIG. 6 shows a side view of the instrument shown in FIG. 2 with the guide sheath and delivery sheath separated.
Figure 7:
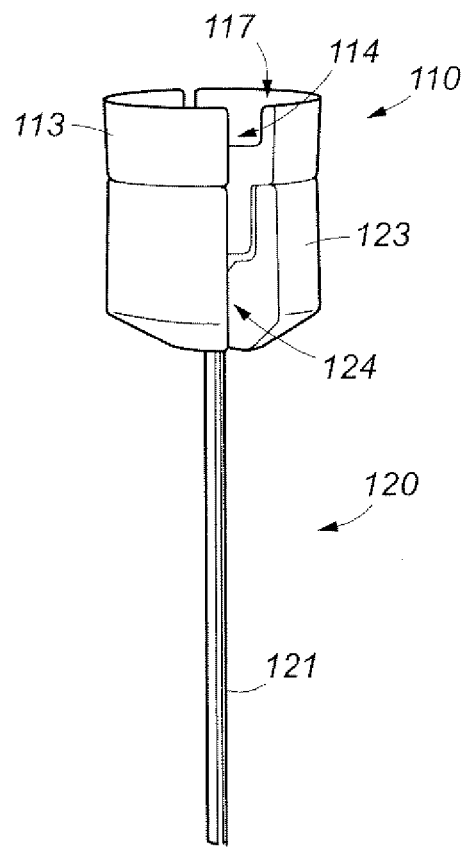
FIG. 7 shows a perspective view of the delivery sheath fully received within the guide sheath of the instrument shown in FIG. 2 without the sensor.

Referring now to FIGS. 6 and 7, as illustrated, the delivery sheath 110 can be slidingly received within the guide sheath 120. As described above, the tubular sheath 111 of the delivery sheath 110 is shaped and sized so as to be able to slide within the tubular sheath 121 of the guide sheath 120, and the spigot 116 of the delivery sheath 110 is shaped and sized so that it can be received within the socket 126 of handle 123 the guide sheath 120. The spigot 116 and socket 126 are shaped so that the spigot can be received in the socket in one angular orientation only. The spigot 116 and socket 126 are configured so that when the spigot 116 is properly received within the socket 126, the slot 112 and 114 of the delivery sheath 110 are aligned with the slots 122 and 124 of the guide sheath. Therefore, as shown in FIGS. 2 and 7, when the delivery sheath 110 is fully received within the guide sheath 120, the slots 112, 114, 122, 144 provide a path between the bore of the tubular sheath 111 of the delivery sheath 110 and the exterior of the assembled instrument.

As shown in FIGS. 2 and 6, the sensor 200 can be part received in the first end 119 of the tubular sheath 111 of the delivery sheath 110 so that the end of the sensor distal to the cable 206 protrudes from the end of the tubular sheath 111. Also as shown, the reference pad 208 can sit within the socket 117 of the handle 113 of the delivery sheath 110. The cable 206 extending between the sensor 200 and the reference pad 208 can extend through the bore of the tubular sheath 111.

Optionally, the handle 113 and/or the reference pad 208, can have temporary attachment means for releasably securing the reference pad within the socket 117 of the handle 113. For example, at least a portion of the raised surface 118 of the socket 117 can be covered in a velcro attachment layer and a portion of the base of the reference pad which is to sit on the base surface 118 can have a corresponding velcro attachment layer so that when the reference pad 208 is located in the socket 117 the reference pad 208 is reasonably held within the handle 113 by the velcro attachment layers.

The length of the tubular sheaths 111, 121 of the delivery sheath 110 and guide sheath 120 are configured so that when the delivery sheath 110 is received within the guide sheath 120, the sensor 200 protrudes from the first ends 119, 128 of the sheaths. The slots 112, 114, 122, 124 are sized so that the cable 206 extending between the sensor 200 and the reference pad 208 can slide through the slots.

Figure 8:
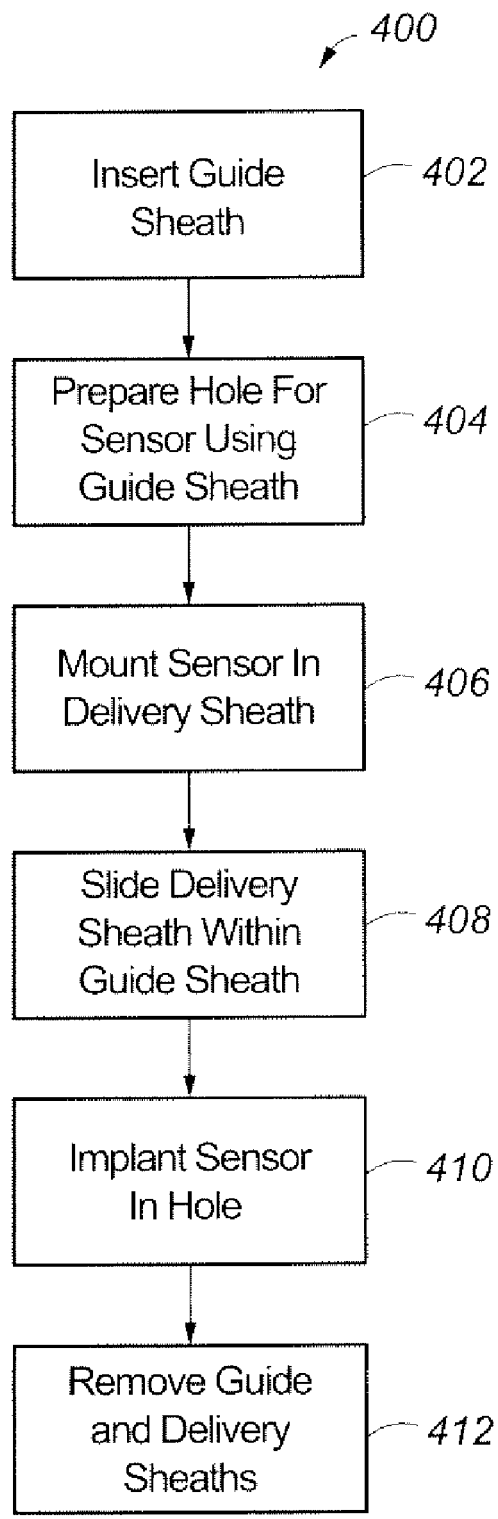
FIG. 8 shows a flowchart illustrating a method of implanting the sensor using the instrument shown in FIGS. 2 to 7.

With reference to FIG. 8 there is shown a flowchart illustrating a method 400 for implanting the sensor 200 shown in FIG. 9 into a bone using the instrument shown in FIGS. 2 to 7.

The method begins at step 402 at which the guide sheath 120 is inserted into the body of a patient, until the teeth 127 of the tubular sheath 121 engage the surface of the bone at the site at which the sensor is to be implanted. The guide sheath 120 can be inserted through the soft tissue surrounding the bone by simply pushing the guide sheath through the soft tissue until the teeth 127 engage the bone. It can in some circumstances be preferable to create an incision in the epidermal layer of the soft tissue, through which the guide sheath 120 is passed, in order to ease the insertion of the tubular sheath 121.

Then at step 404, the hole into which the sensor is to be implanted is prepared. This step comprises inserting the drill bit 300 through the tubular sheath 121 of the guide sheath 120 until the cutting end 301 of the drill bit engages the surface of the bone. A rotational force is then applied to the drill bit 300 by an external tool and applying an axial force to push the drill bit into the bone as it rotates, thereby creating a hole in the bone. The act of rotating and pushing the drill bit 300 continues until the drill bit is prevented from further sliding through the tubular sheath 121 of the guide sheath due to the flange 303 contacting the second end 129 of the tubular sheath. The drill bit 300 is then removed from the guide 120. The guide sheath 120 is retained in its position so that the cutting teeth 127 remain engaged with the bone. As will be understood, if the sensor to be implanted is of the type which does not require a hole to pre-formed in the bone, then step 404 can be omitted.

Then at step 406, the sensor 200 is mounted in the delivery sheath 110. As described above, this can be done by partially receiving the sensor 200 at the second end of the tubular sheath 111 of the delivery sheath 110 so that the end of the sensor distal to the cable 206 protrudes from the end of the tubular sheath. The cable 206 can then be fed through the slot 112 in the delivery sheath 111 so that the cable 206 extends through the bore of the tubular sheath 111. The reference pad 208 can then be placed in the socket 117 of the handle 113.

At step 408, the delivery sheath is slid into the guide sheath 120 in the direction illustrated by arrow A in FIG. 6. Then at step 410, the sensor is implanted in the pre-drilled hole by pushing the delivery sheath 110 through the guide sheath 120 until the sensor 200 has been received within the hole. Once the sensor 200 has been received in the hole, the resiliently deformable jacket will be compressed. As a result, the elastic property of the material of the jacket urges the walls of the body of the jacket against the inner walls of the hole so as to provide a retaining force helping to hold the sensor within the hole. As will be understood, if the sensor is not of the press-fit type described above in relation to FIG. 9, then step 410 will be different. For example, if the sensor has a screw thread for engaging the bone, then at step 410, then sensor can be rotated and forced into the bone until the sensor is anchored within the bone.

At step 412 the guide 120 and delivery 110 sheaths can be removed from the body of the patient. This step includes the steps of removing the reference pad 208 from the socket 117 in the handle 113 of the delivery sheath 110, and then freeing the cable 206 from within the bore of the tubular sheath 111 of the delivery sheath 110. In order to remove the cable 206 from within the delivery sheath 110 and the guide sheath 120, the cable can be fed through the slots 112, 114, 122, 124 of the tubular sheaths 111, 121 and the handles 113, 123. The guide 120 and delivery 110 sheaths can then be removed from the sensor 200 and the tissue surrounding the bone by pulling the guide and delivery sheaths in an direction away from the sensor, along the axes of the guide and delivery sheaths (i.e. in a direction opposite to that shown by arrow A in FIG. 6). The retaining force provided by the jacket 202 of the sensor 200 in the hole is greater than the retaining force keeping the sensor in the tubular shaft 111 of the delivery shaft 110 so that upon pulling of the guide 120 and delivery 110 sheaths, the sensor 200 remains in the hole. Once the guide 120 and delivery 110 sheaths have been removed from the body, any cable 206 still retained within the bore of the tubular sheath 111 of the delivery sheath can be fed through the slots 112, 122 in the tubular sheaths 111, 121 so as to fully free the sensor, cable and reference pad from the guide sheath 120 and delivery sheath 110.

Optionally, the reference pad can be temporarily secured to the skin of the patient through the use of a bonding material such as an adhesive, for example provided on one of the flat surfaces of the reference pad 208. A further optional step is to secure the cable 206 to the skin of the patient in order to try to ensure that the cable does not get accidentally caught, or pulled, during the medial procedure. For example, the cable 206 can be taped to the skin of the patient using adhesive tape.

The invention claimed is:

1. An instrument for implanting a sensor in a body part of a subject, comprising:
    a guide sheath having a first end and a second end, a bore extending along the length of guide sheath between the first end and the second end, a guide handle located at the second end and extending about the circumference of the guide sheath, and a slot extending along the length between the first end and the second open end and through the guide handle;
    a delivery sheath having a first end and a second end, a bore extending along the length of the delivery sheath between the first end and the second end, a delivery handle located at the second end and extending about the circumference of the delivery sheath, a slot that extends along its length between the first end and the second end, wherein the delivery sheath is configured to be slidably disposed within the bore of the guide sheath;

a sensor having a cord extending therefrom, the sensor configured to be mounted on the first end of the delivery sheath and, when assembled with the delivery sheath, having the cord extending from the sensor within the delivery sheath bore; and a reference pad attached to the cord, the reference pad being configured to be attached to the body of the subject, and farther being configured to be at least partially disposed within the delivery sheath handle;

wherein the slots of the guide and delivery sheaths are configured to be aligned to allow the cord to be removed through the slot in the guide sheath; and wherein when the guide sheath, the delivery sheath, the sensor and the reference pad are assembled, the delivery sheath is partially disposed within the guide sheath, and the reference pad is matingly engaged with the delivery sheath, and the guide handle and the delivery handle have inter-engaging formations that are shaped such that the delivery sheath can only be fully received in the guide sheath when the slots of the guide sheath and the delivery sheath are aligned.

2. The instrument of claim 1, wherein the guide sheath has teeth at the first end of the guide sheath configured and arranged to engage the surface of the body part.

3. The instrument of claim 1, wherein the formations of the handles facilitate self-alignment of the slots of the guide sheath and the delivery sheath.

4. The instrument of claim 3, wherein one of the guide sheath handle and the delivery sheath handle includes a non-circular socket and the other includes a spigot configured to be received in the socket, the spigot and socket being contoured to facilitate self-alignment of the guide sheath and the delivery sheath.

5. An instrument for implanting a sensor in a body part of a subject, comprising:

a guide sheath having a first end and a second end, a bore extending along the length of guide sheath between the first end and the second end, a guide handle located at the second end, and a guide slot extending along the length of the guide sheath between the first end and the second open end; and a delivery sheath having a first end and a second end, a bore extending along the length of the delivery sheath between the first end and the second end, a delivery handle located at the second end, a delivery slot that extends along the length of the delivery sheath between the first end and the second end, at least a portion of the delivery sheath being slidably disposable within the bore of the guide sheath; and a sensor having a cord extending therefrom, the sensor configured to be mounted on the first end of the delivery sheath and, when assembled with the delivery sheath, having the cord extending from the sensor within the delivery sheath bore;

wherein the guide handle and the delivery handle have inter-engaging formations that are shaped such that the delivery sheath can only be fully received in the guide sheath when the guide slot and the delivery slots are aligned.

6. The instrument of claim 5, wherein the guide slot and delivery slot are configured such that, when the guide slot and the delivery slot are aligned, the cord is removable through the guide slot.

7. The instrument of claim 5, comprising a reference pad attached to the cord, the reference pad being configured to be attached to the body of the subject.

8. The instrument of claim 7, wherein the reference pad is configured to be at least partially disposed within the delivery sheath handle.

9. The instrument of claim 5, wherein the guide handle extends about the circumference of the guide sheath.

10. The instrument of claim 5, wherein the delivery handle extends about the circumference of the delivery sheath.

11. The instrument of claim 5, wherein the guide slot extends through the guide handle.

12. The instrument of claim 5, wherein the delivery slot extends through the delivery handle.

13. The instrument of claim 7, wherein, when the guide sheath, the delivery sheath, the sensor and the reference pad are assembled together, the delivery sheath is partially disposed within the guide sheath, and the reference pad is matingly engaged with the delivery sheath.

* * * * *

UNITED STATES PATENT AND TRADEMARK OFFICE
CERTIFICATE OF CORRECTION

PATENT NO. : 7,585,302 B2 Page 1 of 1
APPLICATION NO. : 11/063018
DATED : September 8, 2009
INVENTOR(S) : Revie et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 767 days.

Signed and Sealed this

Fourteenth Day of September, 2010

David J. Kappos
*Director of the United States Patent and Trademark Office*